US007873412B2

(12) United States Patent
Wedan (10) Patent No.: US 7,873,412 B2
(45) Date of Patent: Jan. 18, 2011

(54) INDUCED CURRENT MEASUREMENT SYSTEMS AND METHODS

(75) Inventor: Steve R. Wedan, Savage, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 533 days.

(21) Appl. No.: 11/680,267

(22) Filed: Feb. 28, 2007

(65) Prior Publication Data
US 2008/0208276 A1 Aug. 28, 2008

(51) Int. Cl.
*A61N 1/00* (2006.01)
(52) U.S. Cl. ............................................. 607/2
(58) Field of Classification Search ................ 600/423, 600/500; 607/9, 63, 2, 27; 623/1.13
See application file for complete search history.

(56) References Cited

U.S. PATENT DOCUMENTS

| | | | |
|---|---|---|---|
| 4,301,804 A | 11/1981 | Thompson et al. |
| 4,379,459 A | 4/1983 | Stein |
| 4,745,284 A | 5/1988 | Masuda et al. |
| 4,991,580 A | 2/1991 | Moore |
| 5,038,785 A | 8/1991 | Blakeley et al. |
| 5,074,309 A | 12/1991 | Gerdt |
| 5,217,010 A | 6/1993 | Tsitlik et al. |
| 5,347,222 A | 9/1994 | Fox et al. |
| 5,540,724 A | 7/1996 | Cox |
| 5,601,607 A | 2/1997 | Adams |
| 5,968,083 A | 10/1999 | Ciciarelli et al. |
| 6,016,446 A | 1/2000 | Belalcazar |
| 6,198,972 B1 | 3/2001 | Hartlaub et al. |
| 6,427,085 B1 | 7/2002 | Boon et al. |
| 6,641,541 B1 | 11/2003 | Lovett et al. |

(Continued)

FOREIGN PATENT DOCUMENTS

EP 1716878 11/2006
WO WO-03037429 5/2003

OTHER PUBLICATIONS

Abi-Abdallah, Dima et al., "Reference signal extraction from corrupted ECG using wavelet decomposition for MRI sequence triggering: application to small animals", *BioMedical Engineering OnLine*, www.biomedical-engineering-online.com/content/5/1/11 Feb. 20, 2006, pp. 1-12.

(Continued)

*Primary Examiner*—George Manuel
*Assistant Examiner*—Robert N Wieland
(74) *Attorney, Agent, or Firm*—Pauly, DeVries Smith & Deffner, L.L.C.

(57) ABSTRACT

In an embodiment, the invention includes a measurement system for measuring induced currents within an implantable medical device undergoing magnetic resonance imaging. The measurement system can include a resistor connected in series with a conductive loop and electronic circuitry configured to generate a signal representative of a voltage differential across the resistor. In some embodiments, the measurement system includes a fiber optic cable configured to transmit the signal away from the area subject to magnetic resonance imaging. In some embodiments, the measurement system includes a transmitter to wirelessly transmit the signal away from the area subject to magnetic resonance imaging. In an embodiment, the invention can include an implantable medical device including a measurement system for measuring induced currents. In an embodiment, the invention can include a method of measuring an induced current in an implantable medical device undergoing magnetic resonance imaging. Other embodiments are described herein.

17 Claims, 7 Drawing Sheets

U.S. PATENT DOCUMENTS

| | | |
|---|---|---|
| 6,925,322 B2 | 8/2005 | Helfer et al. |
| 6,954,674 B2 | 10/2005 | Connelly |
| 7,015,393 B2 | 3/2006 | Weiner et al. |
| 7,020,517 B2 * | 3/2006 | Weiner ............ 607/4 |
| 7,038,601 B2 | 5/2006 | Uutela et al. |
| 7,050,855 B2 | 5/2006 | Zeijlemaker et al. |
| 7,076,283 B2 | 7/2006 | Cho et al. |
| 7,082,328 B2 | 7/2006 | Funke |
| 7,091,412 B2 | 8/2006 | Wang et al. |
| 7,123,013 B2 | 10/2006 | Gray |
| 2002/0163333 A1 | 11/2002 | Schlicker et al. |
| 2003/0083570 A1 | 5/2003 | Cho et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0176897 A1 * | 9/2003 | Stessman ............ 607/27 |
| 2004/0088012 A1 * | 5/2004 | Kroll et al. ............ 607/9 |
| 2004/0098093 A1 * | 5/2004 | DiCarlo ............ 623/1.13 |
| 2004/0135571 A1 | 7/2004 | Uutela et al. |
| 2004/0263172 A1 | 12/2004 | Gray et al. |
| 2005/0070975 A1 | 3/2005 | Zeijlemaker et al. |
| 2006/0155268 A1 * | 7/2006 | Amir et al. ............ 606/21 |
| 2006/0293591 A1 * | 12/2006 | Wahlstrand et al. ......... 600/423 |
| 2007/0191914 A1 * | 8/2007 | Stessman ............ 607/63 |
| 2008/0147135 A1 | 6/2008 | Hareland |
| 2008/0195180 A1 | 8/2008 | Stevenson et al. |

OTHER PUBLICATIONS

Fontaine, John M. et al., "Rapid Ventricular Pacing in a Pacemaker Patient Undergoing Magnetic Resonance Imaging", *PACE*, vol. 21 Jun. 1998, pp. 1336-1339.

Luechinger, Roger et al., "In Vivo Heating of Pacemaker Leads During Magnetic Resonance Imaging", *European Heart Journal, The European Society of Cardiology* 2004, pp. 1-8.

"International Search Report from International application No. PCT/US2008/055127, mailed Oct. 8, 2008".

"File History for co-pending U.S. Appl. No. 11/684,419, "MRI Compatible Implantable Medical Devices and Methods" (183 pages)".

"International Search Report from International application No. PCT/US2008/056015, mailed Jul. 17, 2008", pp. 1-17.

EP Office Action for related pending application No. 08730844.1, mailed Mar. 19, 2010 (2 pages).

File History for co-pending U.S. Appl. No. 11/686,159, filed Mar. 14, 2007, downloaded from USPTO Website May 5, 2010 (99 pages).

* cited by examiner

INDUCED CURRENT MEASUREMENT SYSTEMS AND METHODS

FIELD OF THE INVENTION

The invention relates to the measurement of induced currents, and more particularly, to the measurement of induced currents within implantable medical devices undergoing magnetic resonance imaging (MRI).

BACKGROUND OF THE INVENTION

Many different types of medical devices are implanted within patients to provide medical therapy. One type of implanted medical device is a cardiac rhythm management device, such as a pacemaker or implantable defibrillator. Cardiac rhythm management devices are used to provide medical therapy to patients who have a disorder related to cardiac rhythm, such as bradycardia.

Magnetic resonance imaging (MRI) is a method of visualizing body tissues of a patient, primarily to identify pathological conditions or to visualize physiological structure for purposes of medical diagnosis and therapy. MRI relies on subjecting the body tissue of interest to a very strong uniform magnetic field, up to about 30,000 gauss, as well as a moderate strength but variable magnetic field of around 200 gauss. In the presence of these uniform and gradient magnetic fields, a radio frequency (RF) pulse is transmitted from a coil to the body tissue. Hydrogen atoms within the body tissue have a magnetic moment and tend to line up with the direction of the applied magnetic fields. Some of these hydrogen atoms will align facing one direction and others will align facing an opposite direction, such that most of the hydrogen atoms facing in alternating directions will tend to cancel each other out. However, a small percentage (but a significant absolute number) of hydrogen atoms will be unbalanced, or not cancelled out. The applied RF pulse tends to cause the unbalanced hydrogen protons to spin, or resonate, in a particular direction and at a particular frequency. When this RF pulse is turned off, the spinning hydrogen protons revert to their earlier, aligned position, and release their excess energy. The RF coil of the MRI machine is capable of detecting this emitted energy and transmitting a corresponding signal to a processor that transforms the signal to an image of the body tissue. Because different tissues have different characteristic responses to the application of the RF pulse in the presence of the magnetic fields, these differences can be utilized to prepare an image showing areas of contrasting tissue types.

MRI techniques have proven to be very effective at diagnosing certain medical conditions and allowing for patients to receive timely, appropriate medical therapy. However, in many cases patients having an implanted medical device are contraindicated for MRI, and therefore may be unable to benefit from the full scope of medical treatments available to them. One problem is that the MRI's RF field can induce a high frequency current within the implanted device, and this high frequency current can result in tissue heating. In certain circumstances the tissue heating can cause serious injury to the patient. Another and potentially very serious problem for a patient having certain implanted medical devices, particularly a cardiac rhythm management device, is the potential for the MRI machine to create a low frequency (less than 20 kHz) induced current (LFIC) in the implanted device. LFIC arises from the interaction between the MRI system's time-varying magnetic gradient fields and any conductive loop associated with the implanted device. LFIC in a CRM device can actually cause pacing of the heart by activating nerve or muscle cells within the heart. In this way, it is possible for the MRI machine to inadvertently pace the patient's heart. The LFIC can also distort the wave shape of intended pacing pulses, possibly resulting in a diminished effectiveness of the pacing pulse. LFIC can further interfere with the pacemaker system's ability to properly sense cardiac activity, possibly resulting in inhibited pacing or pacing that is too rapid.

Given the concerns regarding the effects of LFIC in an implanted medical device, it is desired that the LFIC in an implanted device undergoing an MRI be capable of being measured and quantified. Measuring the LFIC in an implantable device may be desirable for the purpose of evaluating the effects of different device designs on the amount of LFIC generated. Measuring LFIC may also be desirable from the perspective of regulatory approval for implanted devices and the need to demonstrate that a particular device is safe for use in a patient undergoing an MRI. For at least these reasons, improved techniques for measuring LFIC in an implantable medical device are needed.

SUMMARY OF THE INVENTION

The invention relates to methods and devices for measuring induced currents within implantable medical devices undergoing magnetic resonance imaging (MRI). In an embodiment, the invention includes a measurement system for measuring induced current in an implantable medical device undergoing magnetic resonance imaging, the measurement system including a resistor connected in series with a conductive loop of the implantable medical device, electronic circuitry configured to generate an electronic signal representative of a voltage differential across the resistor and to generate an optical signal corresponding to the electronic signal, and a fiber optic cable configured to transmit the optical signal away from an area subject to magnetic resonance imaging.

In an embodiment, the invention includes a measurement system for measuring induced current in an implantable medical device undergoing magnetic resonance imaging, the measurement system including a resistor connected in series with a conductive loop of the implantable medical device, electronic circuitry configured to generate an electronic signal representative of a voltage differential across the resistor, and a transmitter for wirelessly transmitting the electronic signal away from an area subject to magnetic resonance imaging.

In an embodiment, the invention includes a method of measuring an induced current in an implantable medical device undergoing magnetic resonance imaging, the method including generating an electronic signal representative of the voltage differential across a resistor connected in series with a conductive loop of the implantable medical device, converting the electronic signal to a corresponding optical signal, transmitting the optical signal through a fiber optic cable to an area not subject to magnetic resonance imaging, and receiving the optical signal in a computing device that is configured to record the signal.

In an embodiment, the invention includes an implantable medical device including a pulse generator, a lead in communication with the pulse generator, the pulse generator and the lead forming part of a conductive loop, and an induced current sensor including a resistor connected in series with the conductive loop, and electronic circuitry configured to generate an electronic signal representative of a voltage differential across the resistor.

The invention may be more completely understood by considering the detailed description of various embodiments of the invention that follows in connection with the accompanying drawings.

BRIEF DESCRIPTION OF THE DRAWINGS

The invention may be more completely understood in connection with the following drawings, in which.

While the invention may be modified in many ways, specifics have been shown by way of example in the drawings and will be described in detail. It should be understood, however, that the intention is not to limit the invention to the particular embodiments described. On the contrary, the intention is to cover all modifications, equivalents, and alternatives following within the scope and spirit of the invention as defined by the claims.

DETAILED DESCRIPTION OF THE INVENTION

A variety of implanted medical devices are used to provide medical therapies to patients. One example of such an implanted medical device is a cardiac rhythm management (CRM) device, used to manage cardiac conditions such as bradycardia and tachycardia. A specific example of a CRM device is a pacemaker, which can include a pulse generator for generating a pacing pulse and one or more leads for delivering the pacing pulse to the cardiac tissue. Pacemakers can be configured to sense the electrical activity of the patient's heart, as transmitted through the leads. In some pacing modes, if the pacemaker does not detect electrical activity above a certain trigger threshold within a certain time interval, the pacemaker will deliver a pacing pulse through the one or more leads to the cardiac tissue. This pacing pulse causes the heart to beat.

Magnetic resonance imaging relies on the creation of time varying magnetic field gradients within a patient's body. The body of a patient undergoing an MRI exam is not subject to a uniform magnetic field, but rather is subject to a magnetic field that is different at each location of the patient's body and that varies continuously with time. Faraday's law states that any change in a magnetic field around a conductive loop will cause a voltage to be induced in the conductive loop, and consequently, cause a current to flow in the conductive loop. As per Faraday's law, the time varying magnetic field gradients in the body of a patient undergoing an MRI procedure generate a voltage, and consequently a current, in any conductive loop present within the time varying magnetic field. In the case of a patient having an implanted CRM device and undergoing an MRI procedure, the time varying magnetic field gradient of the MRI machine creates the required changing magnetic field and the implanted pacemaker or other cardiac rhythm management device forms the conductive loop. The induced currents can include low frequency induced currents (LFICs), such as at a frequency of less than 20 kHz, that can interfere with the functioning of an implanted medical device. For example, it is possible that LFIC could cause pacing of the heart by activating nerve or muscle cells within the heart. In this way, it may be possible for the MRI machine to inadvertently pace the patient's heart. The LFIC can also distort the waveshape of intended pacing pulses, possibly resulting in a diminished effectiveness of the pacing pulse. LFIC can further interfere with the pacemaker system's ability to properly sense cardiac activity, possibly resulting in inhibited pacing or rapid pacing.

Figure 1:
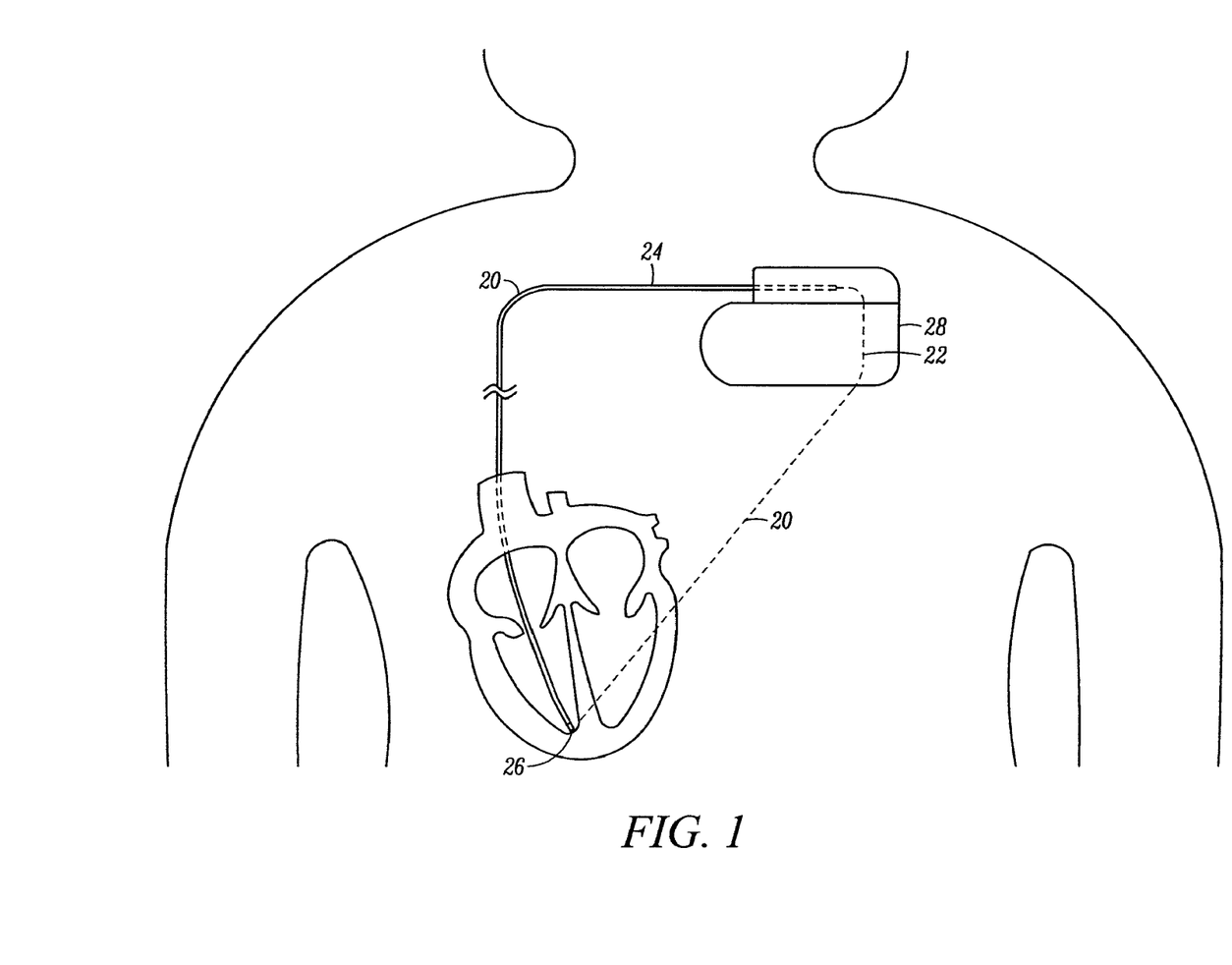
FIG. 1 is a schematic view of a conductive loop formed in an implanted unipolar cardiac pacing device.

In a unipolar pacemaker system such as that depicted in FIG. 1, a loop 20 is formed from the pacemaker internal circuitry 22, through the lead 24 to the electrode 26 in contact with cardiac tissue, and then through body tissue back to the pacemaker housing 28. The area enclosed by this loop is significant and therefore a substantial amount of LFIC can be generated within this loop by the time varying magnetic field gradients of an MRI system.

Figure 2:
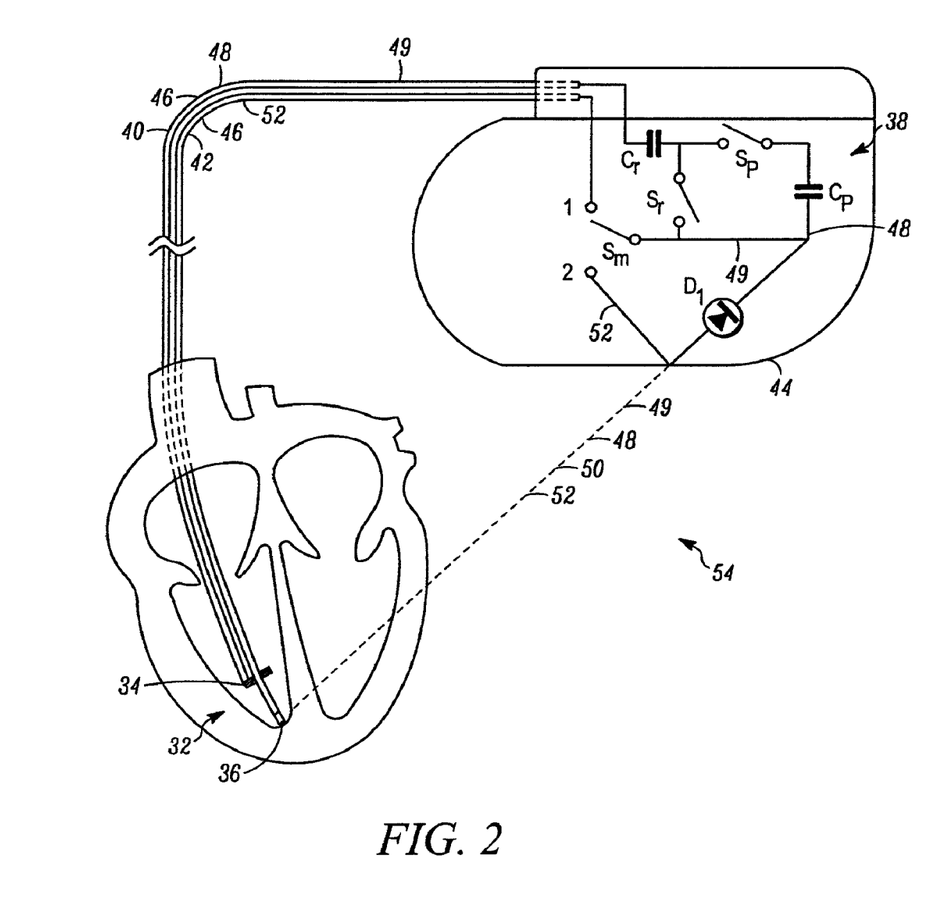
FIG. 2 is a schematic view of a conductive loop formed in an implanted bipolar cardiac pacing device.

Conductive loops can also be created in the context of bipolar pacing systems. FIG. 2 shows a simplified schematic diagram of some aspects of a typical bipolar pacemaker system. Bipolar pacemaker 54 includes a tip and ring electrode 32, where the tip electrode 34 and ring electrode 36 are each implanted in cardiac tissue, but are separated by a relatively small distance from each other. Pacemaker 54 can include various circuitries, such as pulse generation circuitry, sensing circuitry, charging circuitry, control circuitry, and the like. Sensing circuitry, charging circuitry, and control circuitry (not shown in FIG. 2) can be constructed according to principles known to those of skill in the art. In FIG. 2, pulse generator 38 includes pacing switch $S_p$, pacing capacitor $C_p$, recharging switch $S_r$, and recharging capacitor $C_r$. A housing 44 is provided that contains pulse generator 38. The housing 44 can be constructed of a conductive material.

As shown in FIG. 2, pulse generator 38 also includes switch $S_m$ for switching between bipolar mode and unipolar mode. To select a unipolar mode of operation, switch $S_m$ is configured to connect the pacemaker housing 44 to the pulse generator 38 circuitry. In the unipolar mode of operation, the tip electrode 34 generally serves as the cathode and the housing 44 itself serves as the anode. In FIG. 2, this occurs where switch $S_m$ connects to terminal 2 of switch $S_m$. To select a bipolar operation mode, switch $S_m$ is configured to connect conductor 42 to the pulse generator 38 circuitry. In the bipolar mode of operation, the tip electrode 34 generally serves as the cathode and the ring electrode 36 generally serves as the anode. In the embodiment of FIG. 2, this occurs when switch $S_m$ connects to terminal 1 of switch $S_m$.

In bipolar capable pacemakers, there is generally more than one conductive loop in which current can be induced. In bipolar mode, a first loop 46 is formed when either switch $S_p$ or switch $S_r$ is closed, the first loop 46 being formed either through switch $S_r$ or capacitor $C_p$ and switch $S_p$, through capacitor $C_r$, through first conductor 40 and tip electrode 34, through cardiac tissue into ring electrode 36, and through second conductor 42 to switch $S_m$. However, first and second conductors 40, 42 are generally very close together, such as disposed together within one lead. Therefore, conductive loops that include both first conductor 40 and second conductor 42 generally enclose a very small area and therefore induced current in these loops is usually insignificant.

However, conductive loops enclosing a relatively large area can also be formed by some bipolar pacemakers. Many bipolar pacemakers include an integrated circuit protection diode $D_1$. Diode $D_1$ allows current to flow from the pacemaker housing 44 into the pulse generator circuitry to the reference potential (ground) of capacitor $C_p$. This is useful to prevent the pacemaker ground from deviating from the pacemaker housing potential. However, this diode $D_1$ can facilitate the formation of conductive loops within the pacemaker. For example, when switch $S_p$ is closed, loop 48 is formed passing through capacitor $C_p$, switch $S_p$, capacitor $C_r$, conductor 40, tip electrode 34, tissue path 50, back to housing 44 and through diode $D_1$. When switch Sr is closed, loop 49 is formed passing through switch Sr, capacitor Cr, conductor 40, tip electrode 34, tissue path 50, back to housing 44 and through diode $D_1$. Loops 48 and 49 can be formed regardless of the position of switch $S_m$.

Furthermore, when switch $S_m$ is in bipolar mode, another conductive loop 52 can be formed regardless of the positions of switches $S_r$ and $S_p$. Conductive loop 52 can be formed passing through second conductor 42, electrode 36, tissue path 50 to housing 44, through diode $D_1$, and back to second conductor 42 through switch Sm. Loops 48, 49, and 52 each enclose an area sufficiently large to make the generation of LFIC during MRI a concern.

Figure 3:
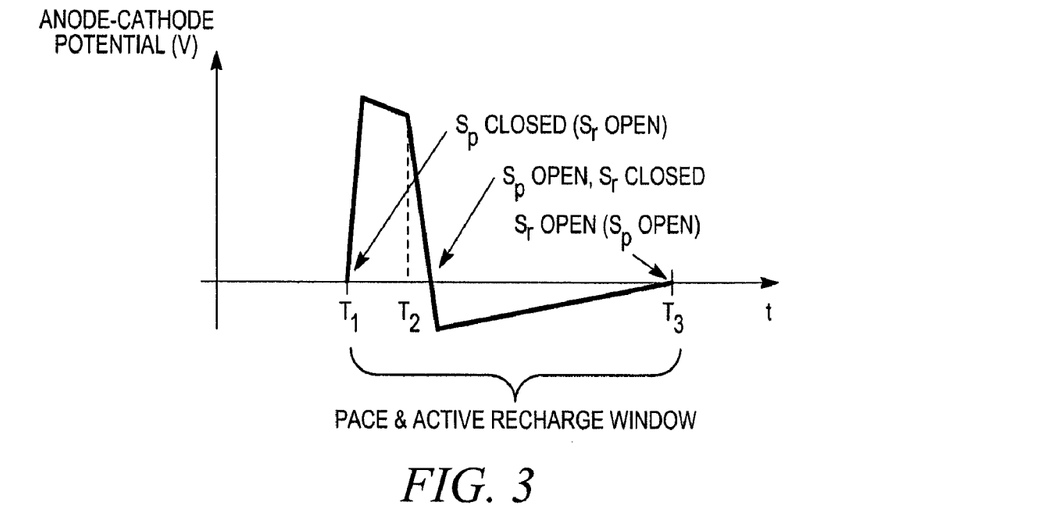
FIG. 3 is a diagram of an idealized pacing pulse.
Figure 4:
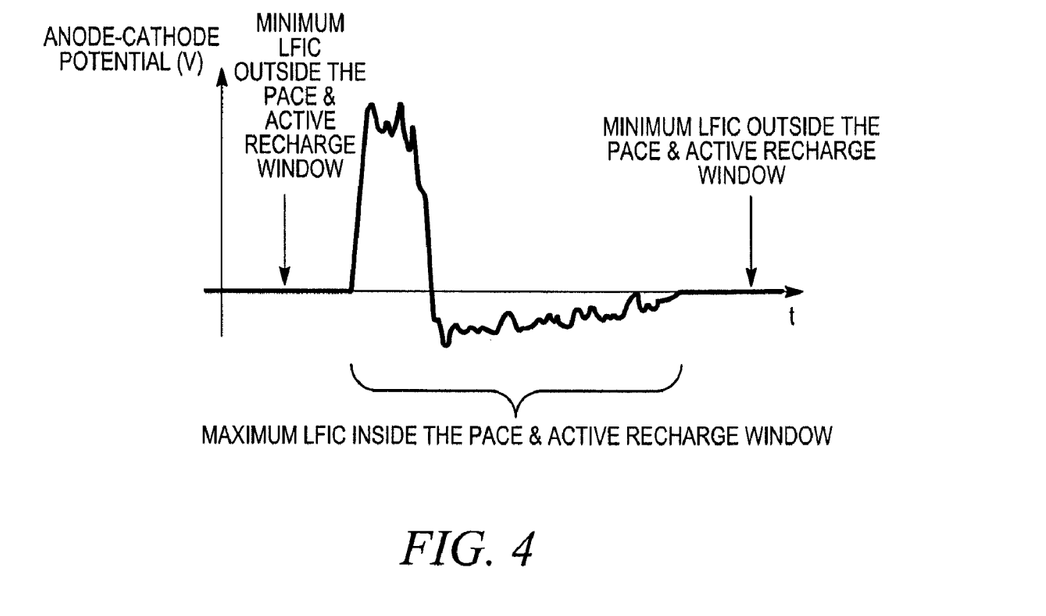
FIG. 4 is a diagram of a pacing pulse affected by low frequency induced current.

LFIC can have harmful effects on the patient. If the induced current is large enough, the current can cause activation of the heart muscle. The induced current can also cause distortion of a pacing pulse sent from the pacemaker through the leads to the heart. For example, FIG. 3 shows an example of an idealized pacing pulse. At a first time $T_1$, a pacing switch is closed causing a current pulse to be delivered through the leads for a period of time, until at time $T_2$ the pacing switch is opened and the current pulse diminishes. Also at time $T_2$, a charging switch is closed to allow charging of a capacitor until time $Tt_3$ when the charging switch is opened. FIG. 4 shows an example of how an idealized pacing pulse can be affected by the presence of LFIC. The current that is induced into the loop will add to or subtract from the voltage of the pacing pulse, resulting in a distorted pulse, such as that seen in FIG. 4. In some cases, the induced distortion may cause the electrical pulse to be insufficient to capture the patient's heart. Alternatively, the induced distortion may result in unreliable sensing of electrical activity in the heart. In some cases, the LFIC may be large enough in magnitude to capture the patient's heart at times other than during the pacing pulse. For example, by forward biasing diode $D_1$, capture outside of the pace and active recharge window can be facilitated. In any case, the LFIC can interfere with the proper operation of the pacing device, possibly causing injury to the patient.

Embodiments of LFIC measurement systems according to the present invention can include features for accurately measuring LFIC. For example, in at least some embodiments, the induced current is measured at two locations very close together to minimize the effect of the gradient magnetic fields on the measurement.

Figure 5:
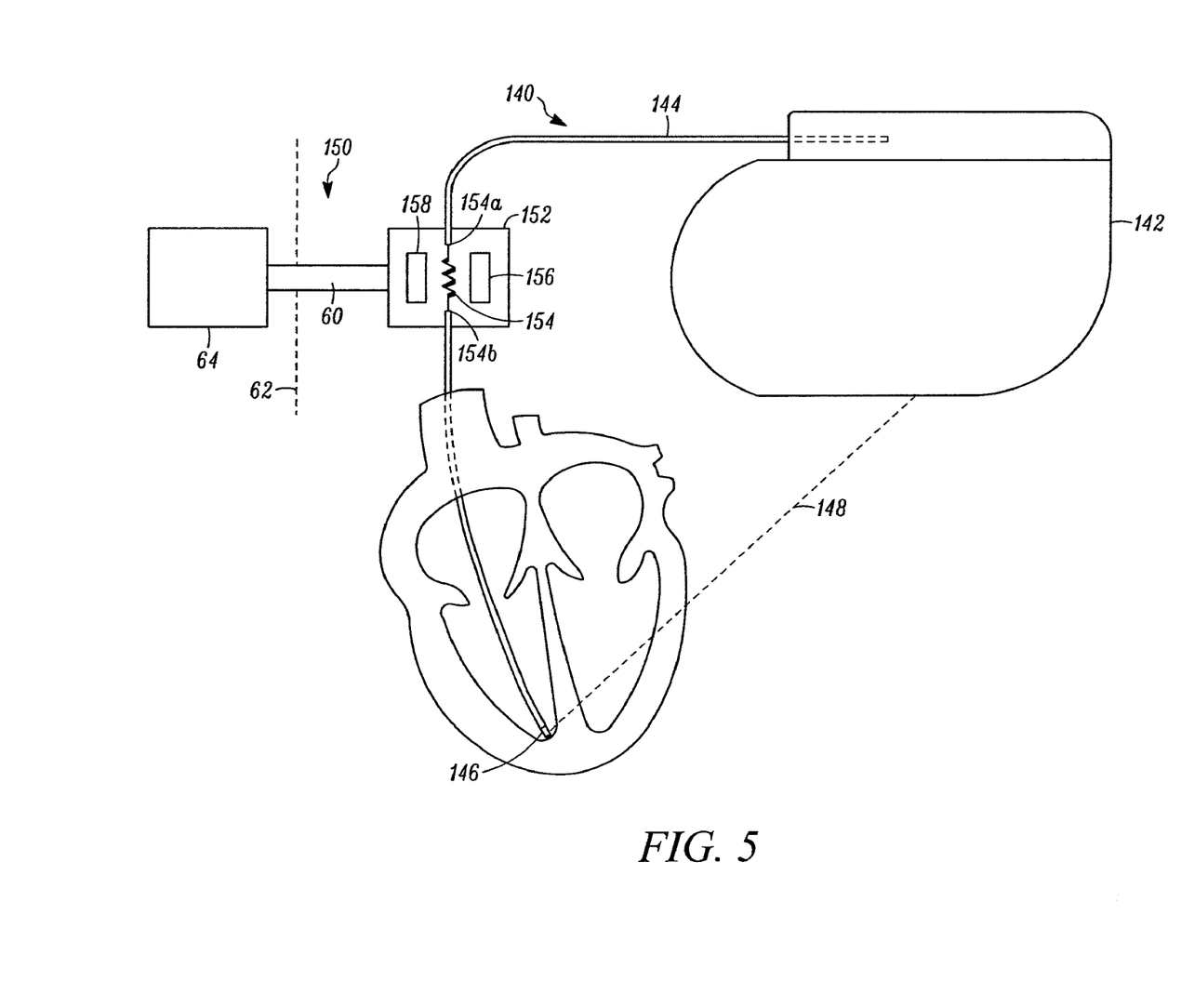
FIG. 5 is a schematic diagram of an induced current measurement system in accordance with an embodiment of the invention, configured for use with an implantable cardiac rhythm management device.

An embodiment of a measurement system constructed according to the principles of the present invention is depicted in FIG. 5. Medical device 140 is implantable in a patient. In the embodiment of FIG. 5, medical device 140 is a unipolar CRM device. However, other devices are usable, such as a bipolar CRM device. The CRM device 140 of FIG. 5 includes a housing 142 containing electronic circuitry, at least one electrically conductive lead 144, and at least one electrode 146 configured to be attached to the patient's cardiac tissue. A conductive loop is formed from housing 142 and associated circuitry, through lead 144 and electrode 146, and through tissue path 148 back to housing 142. An induced current measurement system 150 is provided that advantageously incorporates two measurement locations very close together, such as on opposite sides of a single small resistor. In one embodiment, the measurement locations are less than 25 mm apart. In another embodiment, the measurement locations are less than 10 mm apart. In yet another embodiment, the measurement locations are less than 5 mm apart. By placing the measurement locations close together, the effect of the magnetic field gradient associated with MRI is greatly diminished.

Induced current measurement system 150 includes a current sensor device 152 positioned in series with the conductive loop associated with implantable medical device 140. In the embodiment of FIG. 5, current sensor device 152 is generally positioned in series with lead 144. Alternatively, current sensor device 152 could be positioned in series between lead 144 and housing 142 and associated circuitry. As another alternative, current sensor device 152 could be positioned in series with lead 144 and disposed within housing 142. By being positioned in series with an element of the conductive loop, any current, including both induced current and, in the case of a CRM, current pulses delivered by the CRM to pace the heart, will pass through sensor device 152. Current sensor device 152 can include a resistor 154, a power supply 156, and sensor electronic circuitry 158. Resistor 154 can be a resistor having very small resistance, on the order of 10 ohms. In other embodiments, however, resistor 154 has a resistance between 1 ohm and 50 ohms.

Figure 6:
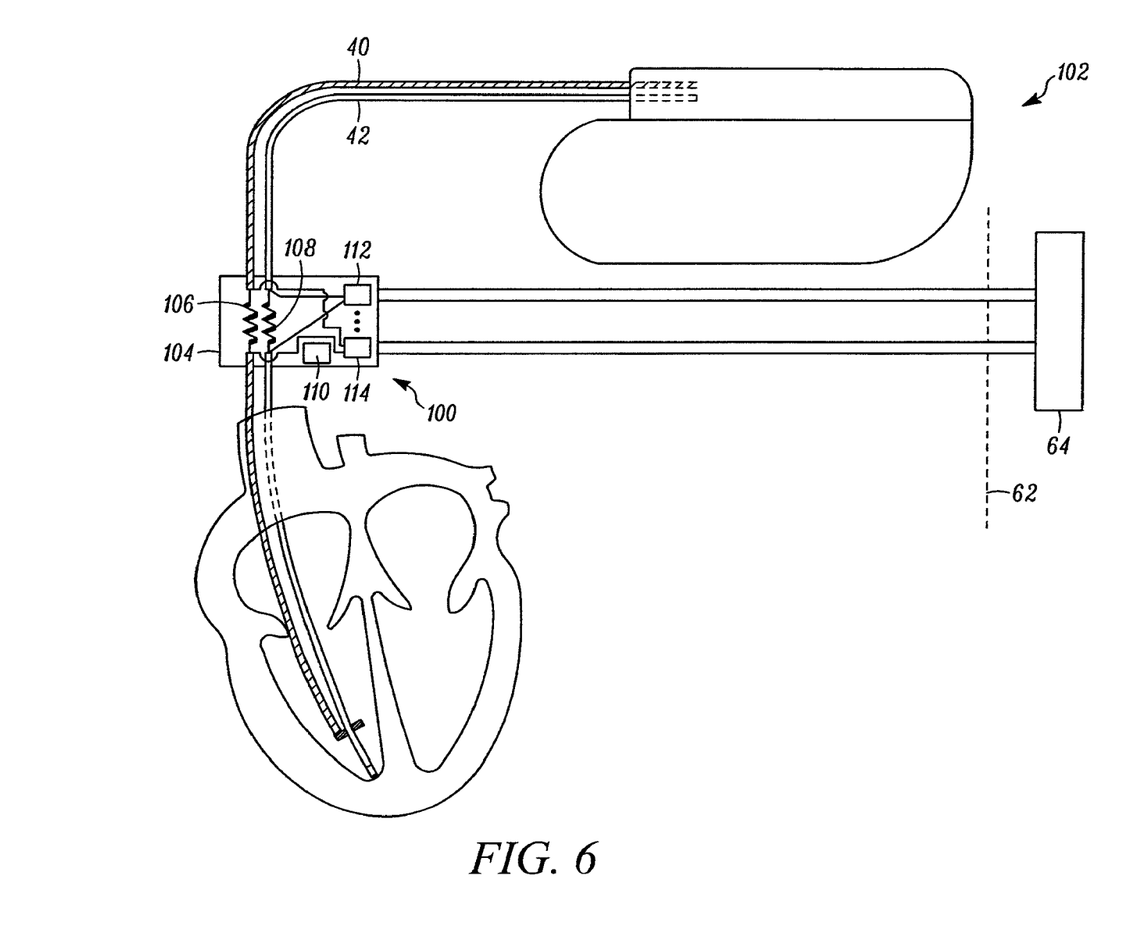
FIG. 6 is a schematic diagram of an induced current measurement system in accordance with an embodiment of the invention, configured for use with a bipolar cardiac rhythm management device.

Another embodiment of a measurement system constructed according to the principles of the present invention is depicted in FIG. 6. Induced current measurement system 100 is configured for use with implantable cardiac rhythm management device 102. Device 102 is configured for bipolar pacing, and is constructed similarly to the device depicted in FIG. 2 with the exception that the induced current measurement system 100 has two independent measurement channels, one channel for each conductor 40, 42. As discussed above, two separate loops may be formed within a bipolar pacing device, where one loop includes first conductor 40 and where the other loop includes the second conductor 42. Therefore, it can be desirable to measure the current within each conductor 40, 42. Induced current measurement system 100 includes current sensor device 104 positioned in series with each of conductors 40, 42. Current sensor device 104 includes first resistor 106 positioned in series with first conductor 40 and second resistor 108 positioned in series with second conductor 42. Current sensor device 104 also includes a power supply 110, first channel sensor electronic circuitry 112, and second channel sensor electronic circuitry 114. Resistors 106, 108 can be resistors having very small resistance, on the order of 10 ohms. In other embodiments, however, resistors 106, 108 have a resistance between 1 ohm and 50 ohms.

Figure 7:
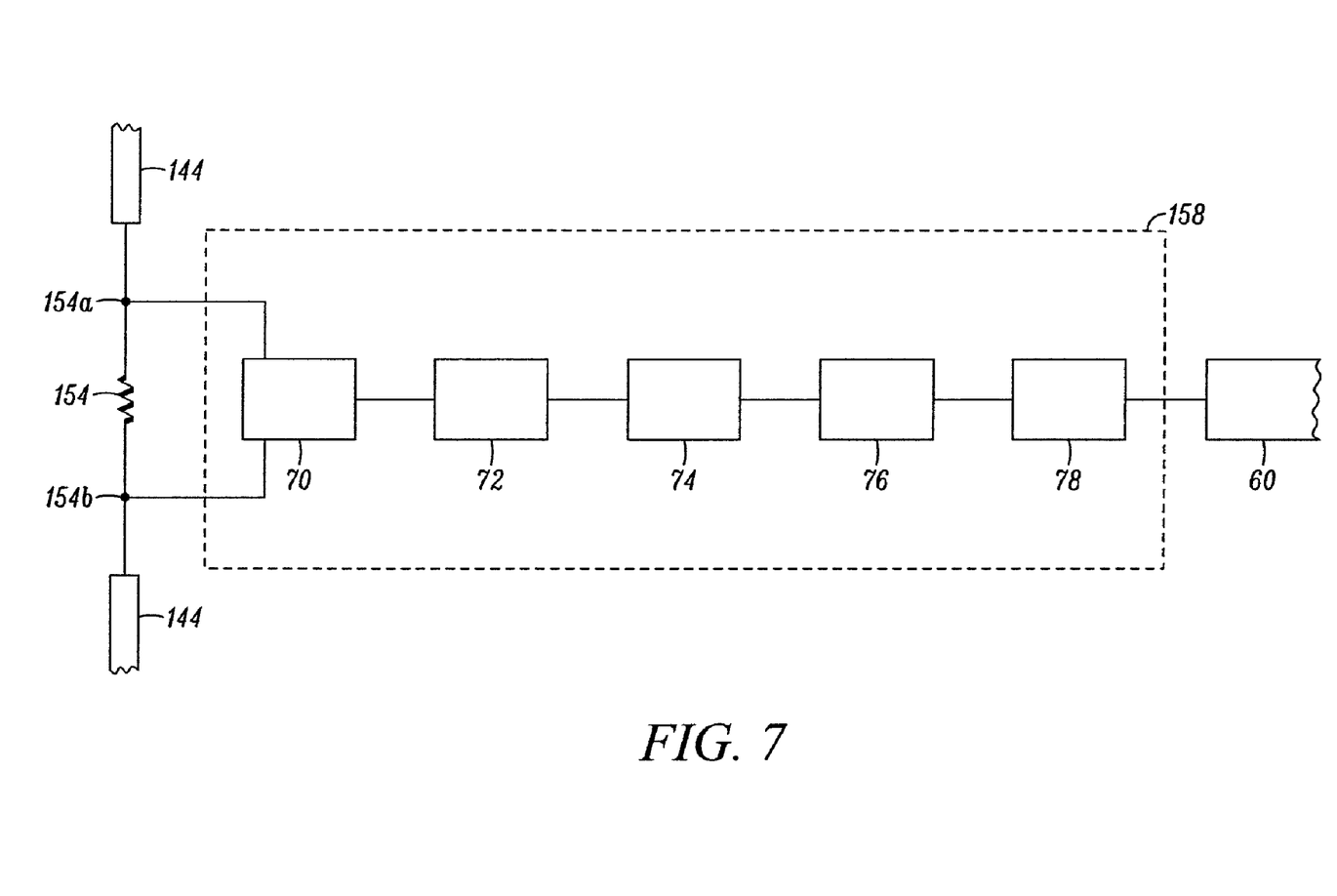
FIG. 7 is a schematic diagram of electronic components within a sensor device.

Each of sensor electronic circuitry 158, first channel sensor electronic circuitry 112, and second channel sensor electronic circuitry 114 can be constructed similarly. For ease of description, reference will only be made to sensor electronic circuitry 158. However, it is to be appreciated that the description of sensor electronic circuitry 158 also applies to first channel sensor electronic circuitry 112 and second channel sensor electronic circuitry 114. Sensor electronic circuitry 158 is configured to generate a signal representative of the induced current within the conductive loop, process that signal, and provide an interface to transmit the signal to an area outside of the MRI environment. One embodiment of sensor electronic circuitry 158 is shown in FIG. 7. In this embodiment, the sensor electronic circuitry 158 includes sensing circuitry 70, amplification circuitry 72, filtration circuitry 74, digitization circuitry 76, and interface circuitry 78. Various aspects of circuitries 70, 72, 74, 76, 78 may occur in physically separate components or circuits, may occur in a single area or component, or may occur in a microprocessor or microcontroller. Various aspects of circuitries 70, 72, 74, 76, 78 may occur sequentially, simultaneously, or in another order.

Sensing circuitry 70 is configured to generate an analog signal corresponding to the voltage differential between a first side 154a of resistor 154 and a second side 154b of resistor 154, where this signal therefore also corresponds to the current passing through resistor 154 according to the relationship defined in Ohm's Law. Digitization circuitry 76 is generally configured to convert the analog signal to a corresponding digital signal, and generally comprises an analog to digital converter. In an embodiment, digitization circuitry 76 has a sampling rate of 20 kHz or higher. In some embodiments, digitization circuitry 76 has a sampling rate of 40 kHz or higher. In an embodiment, digitization circuitry 76 has a sampling resolution of at least 8 bits. Although digitization circuitry 76 can have a different relationship with other circuitries 70, 72, 74, 78 and occur in different orders, in some embodiments digitization occurs as close to the signal generation as possible to limit signal interference and degradation from the MRI magnetic fields. Amplification circuitry 72 is generally configured to amplify the signal generated in the sensing circuitry 70. Filtration circuitry 74 is configured to filter the signal as necessary. In one embodiment, filtration circuitry 74 is configured to achieve a differential signal bandwidth of 15 kHz, high common mode rejection of around 80 dB, and sufficient common mode electromagnetic interference filtering to avoid corruption from rectified high frequency fields such as the MRI's RF field. Interface circuitry 78 is configured to interface with the environment outside of the MRI machine, generally including transmitting the current signal and receiving start and stop instructions. In an embodiment, the interface circuitry 78 includes an optical transmission device, such as a light emitting diode, for converting an electronic signal to an optical signal. Interface circuitry 78 may also perform other functions related to data transmission, such as data compression, coding, or modulation. In some embodiments, particularly embodiments having more than one measurement channel, interface circuitry 78 includes a universal asynchronous receiver/transmitter (UART) for managing the transmission of the digital signal. In one embodiment, a bi-phase UART is provided for digital coding and modulation for transmission over a fiber optic channel. A UART typically is provided to convert parallel data streams, such as data streams from two measurement channels, to a serial data stream for transmission. Each of these circuitries (70, 72 74, 76, 78) can be constructed according to general principles known to those of skill in the art. Further, power supply 156 is incorporated as necessary for the functioning of these circuitries.

In some embodiments, a fiber optic cable 60 is provided that is in signal communication with interface circuitry 78. In some embodiments, two or more fiber optic cables 60 are provided. Referring back to FIG. 5, each fiber optic cable 60 can be configured to pass out of the MRI machine and through a magnetic shielding wall 62 that defines the limits of the MRI testing environment. On the opposite side of shielding wall 62, fiber optic cable 60 is in signal communication with a computing device 64.

In other embodiments interface circuitry 78 is configured to wirelessly transmit the data signal out of the MRI environment. For example, interface circuitry 78 may include a wireless transmitter, such as a radio frequency transmitter, for transmitting the data signal out of the MRI environment.

Referring back to FIG. 5, in one embodiment, computing device 64 is a digital computer configured to receive optical signals transmitted through fiber optic cable 60, convert the optical signals to digital signals, and process the digital signals. In some embodiments, computing device 64 is configured to process the signal to calculate an induced current level within the implantable device 140 that corresponds to the measured voltage differential. For example, the computing device 64 may correlate the received optical signal to a voltage differential across resistor 154, and divide this voltage differential by the resistance of the resistor 154 to determine the amount of current flowing within the conductive loop of device 140.

In an embodiment, computing device 64 includes an interface unit that is configured to receive an optical data stream, perform other functions such as error correction and channel demultiplexing, and to communicate the data stream to a digital computer for further processing. In yet another embodiment, computing device 64 includes an interface unit that is configured to receive wireless signals from transmission circuitry 78. In an embodiment, an interface unit is separate from a digital computer, and includes a microcontroller, a fiber optic transmit and receive module, a UART, and a USB interface for establishing a communication channel with the digital computer. In another embodiment, computing device 64 and an interface unit are not separate components. In yet another embodiment, computing device 64 is configured to receive input and generate commands, such as start or stop, that may be transmitted through fiber optic cable 60 to transmission circuitry 78. In one embodiment, computing device 64 consists of a single device. In other embodiments, computing device 64 consists of more than one device, where the various devices function together.

In some embodiments, the computing device 64 is configured to create a representation of the induced current within the implantable medical device, such as a waveform or a depiction of the amount of induced current. In this manner, the characteristics of the LFIC within the implanted device can be determined. This information can be used to evaluate various device designs, such as for determining the effect a proposed device design has on LFIC. This information can also be used to determine whether there is a risk of adverse effects when a patient having an implanted device is subjected to an MRI examination, and also for the purposes of demonstrating the safety of the implanted device and attaining regulatory approval for the use of the implanted device in an MRI machine.

The current measurement system 150 and implantable medical device 140 may be positioned either in vitro or in vivo for testing purposes, as dictated by the nature of the study being performed. If system 150 and device 140 are in vitro, it is necessary to simulate a conductive tissue path 148. For example, tissue path 148 could be simulated by a resistor between electrode 146 and housing 142 that is comparable to the resistance of body tissue between these two points. The implantable medical device 140 and the current sensor device 152 can then be placed within the MRI machine, with fiber optic cable 60 passing out of the MRI machine and out of the MRI room. The MRI machine is then activated and utilized in a customary manner.

Embodiments of the invention can also include other features. By way of example, in some embodiments, the measurement circuitry does not include any loops that could themselves be subject to current induction. In some cases, the measurement circuitry includes no ferromagnetic materials in order to minimize the influence of the magnetic fields in the MRI. In some embodiments, the measurement circuitry includes analog circuitry that is physically very small to minimize signal distortion. In some embodiments, the system includes one or more non-conductive communication channels for transmitting sensed current data out of the MRI environment without being subject to magnetic interference.

Figure 8:
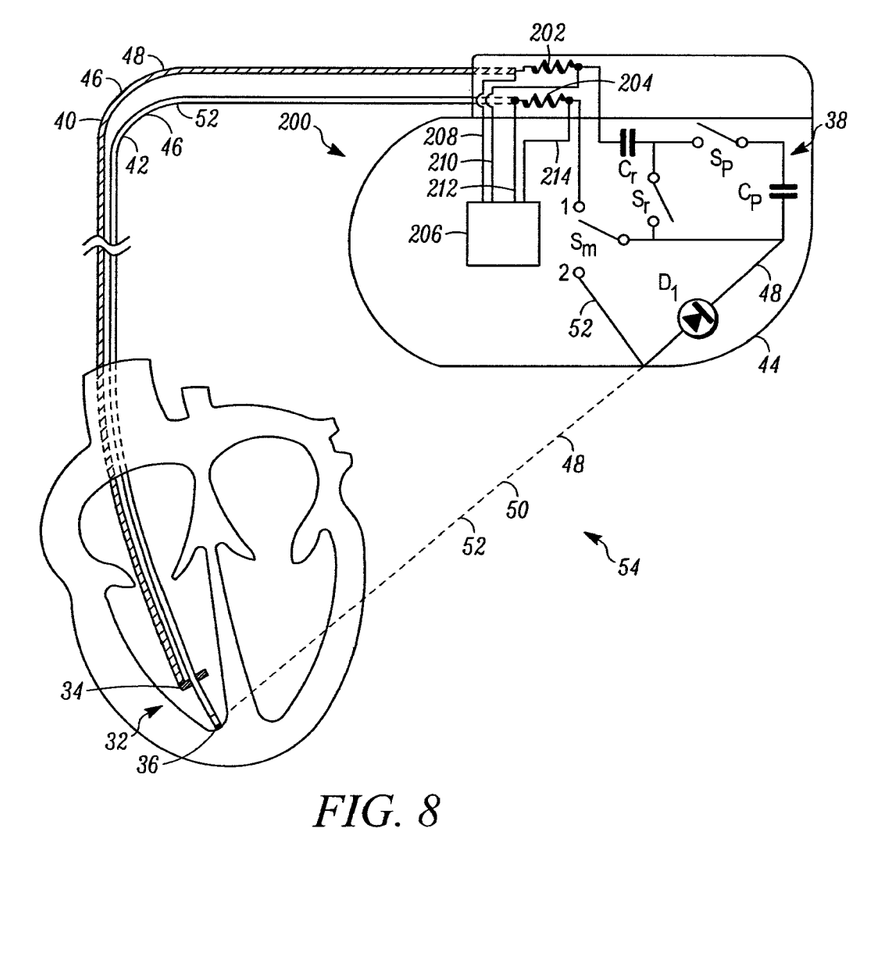
FIG. 8 is a schematic diagram of an alternative embodiment of an induced current measurement system for use with an implantable cardiac rhythm management device.

Yet another embodiment is depicted in FIG. 8. The embodiment of FIG. 8 includes elements that are similar to the embodiment depicted in FIG. 2, such as a pulse generator 38 inside a housing 44, and has additional components that function similarly to the embodiment depicted in FIG. 2. However, the embodiment of FIG. 8 further includes an induced current measurement system 200 within the housing 44. In one embodiment, the induced current measurement system 200 includes a first resistor 202 positioned in series with first conductor 40 and a second resistor 204 positioned in series with second conductor 42. Other embodiments have only one of first resistor 202 and second resistor 204. By positioning either of first resistor 202 and second resistor 204, or both, in series with an element of the conductive loop such as first or second conductors 40, 42, any current, including both induced current and, in the case of a CRM, current pulses delivered by the CRM to pace the heart, will pass through the resistors 202, 204. Current sensor system 200 includes voltage sensing leads 208, 210, 212, 214 that transmit the voltage at each side of resistor 202, 204, respectively, to sensor electronic circuitry 206. Resistors 202, 204 can be resistors having relatively small resistance, on the order of 10 ohms. In other embodiments, however, resistors 202, 204 have a resistance between 1 ohm and 50 ohms.

Sensor electronic circuitry 206 senses the voltage at each side of resistors 202, 204, as present. Based on the measured voltage differential, and also the known resistance of resistors 202, 204, sensor electronic circuitry can determine the amount of current in first and second conductors 40, 42, respectively. In the embodiment of FIG. 8, sensor electronic circuitry 206 is further configured to store or record the measured voltage differentials or currents. The sensor electronic circuitry 206 may also include telemetry capabilities to allow for wireless communication between the sensor electronic circuitry 206 and an external device. The stored data can be transmitted to the external device as desired or convenient, such as after a patient completes an MRI examination or at a patient's regularly scheduled check-up. In other embodiments, the sensor electronic circuitry 206 can wirelessly transmit the voltage or current data to an external device in real time while a patient undergoes an MRI procedure.

It will be appreciated that an induced current measurement system can also be located within a header of an implantable device.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

The above specification provides a complete description of the structure and use of the invention. Since many of the embodiments of the invention can be made without parting from the spirit and scope of the invention, the invention resides in the claims.

What is claimed is:

1. A measurement system for measuring induced current in an implantable medical device undergoing magnetic resonance imaging, the measurement system comprising:
   (i) a resistor connected in series with a conductive loop of the implantable medical device, wherein the conductive loop comprises a pulse generator and a lead;
   (ii) electronic circuitry configured to generate an electronic signal representative of a voltage differential across the resistor and to generate an optical signal corresponding to the electronic signal;
   (iii) an area shielded from magnetic fields generated by magnetic resonance imaging defined by a magnetic shielding wall; and
   (iv) a fiber optic cable configured to transmit the optical signal away from an area subject to magnetic resonance imaging, the fiber optic cable configured to transmit the optical signal to the area shielded from magnetic fields generated by magnetic resonance imaging.

2. The measurement system of claim 1, further comprising a computing device configured to receive the optical signal.

3. The measurement system of claim 1, wherein the resistor has a resistance of between about 1 ohms and about 50 ohms.

4. The measurement system of claim 1, the implantable medical device comprising a cardiac rhythm management device comprising a lead in communication with a pulse generator.

5. The measurement system of claim 3, the resistor connected in series between the pulse generator and the lead.

6. The measurement system of claim 1, the electronic signal representing a voltage differential between two locations less than 5 mm apart.

7. The measurement system of claim 1, the electronic circuitry comprising an analog to digital converter.

8. The measurement system of claim 1, the electronic circuitry comprising a light emitting diode for generating the optical signal.

9. The measurement system of claim 2, wherein the computing device is further configured to determine an induced current level from the voltage differential signal.

10. The measurement system of claim 1, the induced current having a frequency of less than about 20 kHz.

11. A method of measuring an induced current in an implantable medical device undergoing magnetic resonance imaging, the method comprising:
   (i) generating an electronic signal representative of the voltage differential across a resistor connected in series with a conductive loop of the implantable medical device, wherein the conductive loop comprises a pulse generator and a lead;
   (ii) converting the electronic signal to a corresponding optical signal;
   (iii) transmitting the optical signal through a fiber optic cable to an area not subject to magnetic resonance imaging, the fiber optic cable configured to transmit the optical signal to an area shielded from magnetic fields generated by magnetic resonance imaging, wherein the area shielded from magnetic fields generated by magnetic resonance imaging defined by a magnetic shielding wall; and
   (iv) receiving the optical signal in a computing device that is configured to record the signal.

12. The method of claim 11, the resistor connected in series between a pulse generator and the lead.

13. The method of claim 11, the electronic voltage differential signal representing the voltage differential between two locations less than 5 mm apart.

14. The method of claim 11, further comprising the step of converting the electronic signal from analog to digital prior to the step of converting the electrical signal to an optical signal.

15. The method of claim 11, wherein the area not subject to magnetic resonance imaging is in a separate room shielded from magnetism generated by magnetic resonance imaging.

16. The method of claim 11, the computing device further configured to determine an induced current level from the voltage differential signal.

17. The method of claim 11, the computing device further configured to convert the optical signal to an electronic signal.

* * * * *